United States Patent
Jang et al.

(10) Patent No.: US 9,372,281 B2
(45) Date of Patent: Jun. 21, 2016

(54) METHOD FOR PREPARING THIOEPOXY-BASED OPTICAL MATERIAL AND POLYMERIZABLE COMPOSITION THEREOF

(71) Applicant: KOC SOLUTION CO., LTD, Daejeon (KR)

(72) Inventors: Dong Gyu Jang, Daejeon (KR); Soo Gyun Roh, Daejeon (KR); Jong Hyo Kim, Daejeon (KR)

(73) Assignee: KOC SOLUTION CO., LTD., Daejeon (KR)

( * ) Notice: Subject to any disclaimer, the term of this patent is extended or adjusted under 35 U.S.C. 154(b) by 0 days.

(21) Appl. No.: 14/373,289

(22) PCT Filed: Jan. 21, 2013

(86) PCT No.: PCT/KR2013/000483
§ 371 (c)(1),
(2) Date: Jul. 18, 2014

(87) PCT Pub. No.: WO2013/109118
PCT Pub. Date: Jul. 25, 2013

(65) Prior Publication Data
US 2014/0336332 A1    Nov. 13, 2014

(30) Foreign Application Priority Data

Jan. 20, 2012 (KR) .................. 10-2012-0006919
Jan. 26, 2012 (KR) .................. 10-2012-0007521

(51) Int. Cl.
| | |
|---|---|
| G02B 1/04 | (2006.01) |
| C07D 409/12 | (2006.01) |
| C08G 18/58 | (2006.01) |
| C08G 18/38 | (2006.01) |
| C08G 18/16 | (2006.01) |
| C08G 18/75 | (2006.01) |
| C08G 75/08 | (2006.01) |
| C08L 81/02 | (2006.01) |
| C07D 331/02 | (2006.01) |

(52) U.S. Cl.
CPC .............. *G02B 1/041* (2013.01); *C07D 409/12* (2013.01); *C08G 18/168* (2013.01); *C08G 18/3874* (2013.01); *C08G 18/3876* (2013.01); *C08G 18/585* (2013.01); *C08G 18/755* (2013.01); *C07D 331/02* (2013.01); *C08G 75/08* (2013.01); *C08L 81/02* (2013.01)

(58) Field of Classification Search
CPC ....... C08G 75/08; C08L 81/02; C08D 331/02
See application file for complete search history.

(56) References Cited

U.S. PATENT DOCUMENTS

| | | | | |
|---|---|---|---|---|
| 6,204,311 | B1 * | 3/2001 | Morijiri et al. ................ | 523/400 |
| 8,013,084 | B2 * | 9/2011 | Ihara et al. ..................... | 526/89 |
| 2005/0124783 | A1 * | 6/2005 | Morijiri et al. ............... | 528/377 |
| 2014/0336332 | A1 * | 11/2014 | Jang et al. ..................... | 524/710 |

FOREIGN PATENT DOCUMENTS

| | | |
|---|---|---|
| JP | 11-352302 | 12/1999 |
| JP | 2005-298742 | 10/2005 |
| KR | 10-1992-0005708 | 7/1992 |
| KR | 10-1993-0006918 | 7/1993 |
| KR | 10-0417985 | 2/2004 |
| KR | 10-2004-0060966 | 2/2007 |
| KR | 10-0681218 | 2/2007 |
| KR | 10-2009-0082719 | 7/2009 |

OTHER PUBLICATIONS

International Search Report dated Apr. 24, 2013 for International Application No. PCT/KR2013/000483.

* cited by examiner

*Primary Examiner* — Michael A Salvitti
(74) *Attorney, Agent, or Firm* — Susan Paik, Esq.

(57) ABSTRACT

The present invention relates to a thioepoxy compound for an optical material, a polymerizable composition including the thioepoxy compound, and a method for producing a thioepoxy optical material by polymerization of the polymerizable composition. The polymerizable composition further includes 4.1 to 15% by weight of 2,3-epoxypropyl(2,3-epithiopropyl)sulfide and/or 2,3-epoxypropyl(2,3-epithiopropyl)disulfide. The thioepoxy optical material is free from color instability, demolding, and polymerization imbalance, which are problems encountered in general thioepoxy optical materials.

17 Claims, No Drawings

METHOD FOR PREPARING THIOEPOXY-BASED OPTICAL MATERIAL AND POLYMERIZABLE COMPOSITION THEREOF

TECHNICAL FIELD

The present invention relates to a thioepoxy optical material. More particularly, the present invention relates to a method for producing a clear, transparent thioepoxy optical material that is substantially free from problems such as color instability, a composition for use in the method, and a thioepoxy compound for use in the composition.

BACKGROUND ART

Plastic lenses are more lightweight, resistant to impact, and easily dyeable than conventional glass lenses. Due to these advantages, plastic lenses have recently been applied to most spectacle lenses. Particularly, plastic lenses typified by diethylene glycol bisallyi carbonate (CR-39) lenses have been applied as general lenses. These lenses with low chromatic aberration are useful in that they give a comfortable field of view, but have been required to have higher refractive index. Korean Patent Publication Nos. 1993-0006918 and 1992-0005708 propose thiourethane lenses manufactured by reacting polythiol compounds with polyisocyanate compounds. Further, Korean Patent Registration No. 10-0681218 proposes a thioepoxy plastic lens.

The thiourethane lenses have the advantages of high refractive index and impact strength but suffer from several problems such as weak surface and depressed center. The Abbe numbers of the thiourethane lenses tend to decrease markedly with increasing refractive index. The thioepoxy lens has the advantages of high refractive index and Abbe number but is likely to be brittle and is not readily dyed. Some attempts to solve the problems of thiourethane lenses and thioepoxy lenses have been proposed. For example, Korean Patent Registration No. 10-0417985 and Japanese Patent Publication No. Hei 11-352302 propose methods for manufacturing lenses by copolymerization of two resins having different properties, i.e. by copolymerization of thioepoxy, polythiol and polyisocyanate compounds.

However, some thioepoxy lenses including thioepoxy compounds as main monomers are still unstable in color. Korean Patent Registration No. 10-0681218 reveals that the purity of a thioepoxy compound converted from an epoxy compound, i.e. the content of by-products of the conversion process in the thioepoxy compound, is a factor affecting the color of lenses. Further, this patent discloses a polymerizable composition including a reduced amount of the by-products and a method for reducing the content of the by-products.

SUMMARY OF THE INVENTION

The present invention has been made in view of the problem of color instability encountered in general thioepoxy lenses including thioepoxy compounds as major monomers, and it is an object of the present invention to provide a method for producing a clear, transparent high quality thioepoxy optical material that is free from problems associated with color, demolding and polymerization imbalance, a polymerizable composition for use in the method, and a thioepoxy compound for use in the polymerizable composition.

The present inventors have unexpectedly found that a thioepoxy compound containing 4.1 to 15% by weight of 2,3-epoxypropyl(2,3-epithiopropyl)sulfide and/or 2,3-epoxypropyl(2,3-epithiopropyl)disulfide, which are intermediate compounds having both 2,3-epoxypropyl and 2,3-epithiopropyl groups as a result of incomplete conversion of an epoxy group to a thioepoxy group in the preparation of the thioepoxy compound, has a better color than a thioepoxy compound containing less than 4% by weight or more than 15% by weight of 2,3-epoxypropyl(2,3-epithiopropyl)sulfide and/or 2,3-epoxypropyl(2,3-epithiopropypdisulfide. The present inventors have also found that an optical material produced using the thioepoxy compound containing 4.1 to 15% by weight of 2,3-epoxypropyl(2,3-epithiopropypsulfide and/or 2,3-epoxypropyl(2,3-epithiopropyl)disulfide undergoes no yellowing, has a good color, and is free from problems associated with demolding and polymerization imbalance. The present invention has been completed based on these findings.

The present invention provides
a polymerizable composition including a thioepoxy compound (A) and a compound (B) formed as a by-product in the preparation of the thioepoxy compound (A) wherein the compound (B) is at least one of 2,3-epoxypropyl(2,3-epithiopropyl)sulfide and 2,3-epoxypropyl(2,3-epithiopropyl)disulfide represented by Formula 1 and is present in an amount of 4.1 to 15% by weight.

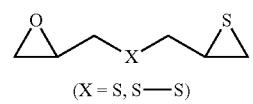

[Formula 1]

(X = S, S—S)

The present invention also provides
a polymerizable composition including the thioepoxy compound. The polymerizable composition may further include a polyisocyanate compound and/or a polythiol compound. The polymerizable composition may further include an olefinic compound as a reactive resin modifier. The polymerizable composition may further include an internal release agent.

The present invention also provides a method for producing a thioepoxy optical material, including polymerizing the polymerizable composition.

The present invention also provides
a thioepoxy optical material obtained by polymerization of the polymerizable composition and an optical lens composed of the optical material.

DETAILED DESCRIPTION

The polymerizable composition of the present invention includes a thioepoxy compound containing 2,3-epoxypropyl (2,3-epithiopropyl)sul fide and/or 2,3-epoxypropyl(2,3-epithiopropyl)disulfide, which are intermediate compounds in the conversion of an epoxy group to a thioepoxy group. By limiting the content of the intermediate compound(s) in the thioepoxy compound to 4 to 15% by weight, the problems of color instability, demolding, and polymerization imbalance encountered in general thioepoxy optical materials can be solved. According to the present invention, a clear, transparent high quality lens can be easily manufactured in high yield. A thioepoxy optical material obtained by the method of the present invention is suitable for use in the manufacture of corrective lenses, sunglass lenses, fashion lenses, photochromic lenses, camera lenses, and lenses for optical units.

Best Mode

The present invention provides a polymerizable composition for a thioepoxy optical material including a thioepoxy compound (A). The polymerizable composition further includes 4.1 to 15% by weight of 2,3-epoxypropyl(2,3-epithiopropyl)sulfide and/or 2,3-epoxypropyl(2,3-epithiopropyl)disulfide represented by the following formula 1, which is formed as a by-product in the preparation of the thioepoxy compound (A). The 2,3-epoxypropyl(2,3-epithiopropyl)sulfide and 2,3-epoxypropyl(2,3-epithiopropyl)disulfide are intermediate compounds formed when an epoxy group is converted to a thioepoxy group in the preparation of the thioepoxy compound. An optical material produced using the polymerizable composition including 4.1 to 15% by weight of at least one of the intermediate compounds has a good color and is free from problems associated with demolding and polymerization imbalance, compared to an optical material produced using the polymerizable composition including less than 4.1% by weight or more than 15% by weight of at least one of the intermediate compounds.

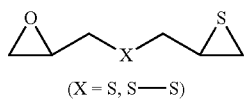

[Formula 1]

(X = S, S—S)

For example, the thioepoxy compound may be selected from: episulfide compounds having an alicyclic skeleton, such as bis(2,3-epithiopropyl)sulfide, bis(2,3-epithiopropyl)disulfide, 2,3-epidithiopropyl(2,3-epithiopropyl)disulfide, 2,3-epidithiopropyl(2,3-epithiopropyl)sulfide, 1,3- and 1,4-bis(β-epithiopropylthio)cyclohexanes, 1,3- and 1,4-bis(β-epithiopropylthiomethyl)cyclohexanes, bis[4-(β-epithiopropylthio)cyclohexyl]methane, 2,2-bis[4-(β-epithiopropylthio)cyclohexyl]propane, and bis[4-(β-epithiopropylthio)cyclohexyl]sulfide; episulfide compounds having an aromatic skeleton, such as 1,3- and 1,4-bis(β-epithiopropylthiomethyl)benzenes, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfine, and 4,4-bis(β-epithiopropylthio)biphenyl; episulfide compounds having a dithiane chain skeleton, such as 2,5-bis(β-epithiopropylthiomethyl)-1,4-dithiane, 2,5-bis(β-epithiopropylthioethylthiomethyl)-1,4-dithiane, 2,5-bis(β-epithiopropylthioethyl)-1,4-dithiane, and 2,3,5-tri(β-epithiopropylthioethyl)-1,4-dithiane; episulfide compounds having an aliphatic skeleton, such as 2-(2-β-epithiopropylthioethylthio)-1,3-bis(β-epithiopropylthio)propane, 1,2-bis[(2-(β-epithiopropylthioethyl)thio]-3-(β-epithiopropylthio)propane, tetrakis(β-epithiopropylthiomethyl)methane, 1,1,1-tris(β-epithiopropylthiomethyl)propane, and bis(β-epithiopropyl)sulfide; and mixtures thereof. As the thioepoxy compound, there may also be used, for example: a halogenated product of a compound having an episulfide group, such as a chlorinated or brominated product of a compound having an episulfide group; an alkylated product of a compound having an episulfide group; an alkoxylated product of a compound having an episulfide group; a nitro-substituted product of a compound having an episulfide group; or a prepolymer modified product of a compound having an episulfide group with a polyhydric alcohol.

The thioepoxy compound is preferably selected from bis(2,3-epithiopropyl)sulfide, bis(2,3-epithiopropyl)disulfide, 2,3-epidithiopropyl(2,3-epithiopropyl)sulfide, 2,3-epidithiopropyl(2,3-epithiopropyl)disulfide, 1,3- and 1,4-bis(β-epithiopropylthio)cyclohexanes, 1,3- and 1,4-bis(β-epithiopropylthiomethyl)cyclohexanes, 2,5-bis(β-epithiopropylthiomethyl)-1,4-dithiane, 2,5-bis(β-epithiopropylthioethylthiomethyl)-1,4-dithiane, 2-(2-(β-epithiopropylthioethylthio)-1,3-bis(β-epithiopropylthio)propane, and mixtures thereof.

The present invention also provides a polymerizable composition including the thioepoxy compound. The polymerizable composition of the present invention may further include a polyisocyanate compound. The polyisocyanate compound may be any compound having at least one isocyanate group and/or at least one isothiocyanate group. Examples of such polyisocyanate compounds include: aliphatic isocyanate compounds, such as 2,2-dimethylpentane diisocyanate, hexamethylene diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl)carbonate, and bis(isocyanatoethyl)ether; alicyclic isocyanate compounds, such as isophorone diisocyanate, 1,2-bis(isocyanatomethyl)cyclohexane, 1,3-bis(isocyanatomethyl)cyclohexane, 1,4-bis(isocyanatomethyl)cyclohexane, dicyclohexylmethane diisocyanate, cyclohexane diisocyanate, methylcyclohexane diisocyanate, dicyclohexyldimethylmethane isocyanate, and 2,2-dimethyldicyclohexylmethane isocyanate; aromatic isocyanate compounds, such as xylylene diisocyanate (XDI), bis(isocyanatoethyl)benzene, bis(isocyanatopropyl)benzene, bis(isocyanatobutyl)benzene, bis(isocyanatomethyl)naphthalene, bis(isocyanatomethyl)diphenyl ether, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4-diphenylmethane diisocyanate, 3,3-dimethyldiphenylmethane-4,4-diisocyanate, bibenzyl-4,4-diisocyanate, bis(isocyanatophenyl)ethylene, 3,3-dimethoxybiphenyl-4,4-diisocyanate, hexahydrobenzene diisocyanate, and hexahydrodiphenylmethane-4,4-diisocyanate; sulfur-containing aliphatic isocyanate compounds, such as bis(isocyanatoethyl)sulfide, bis(isocyanatopropyl)sulfide, bis(isocyanatohexyl)sulfide, bis(isocyanatomethyl)sulfone, bis(isocyanatomethyl)disulfide, bis(isocyanatopropyl)disulfide, bis(isocyanatomethylthio)methane, bis(isocyanatoethylthio)methane, bis(isocyanatoethylthio)ethane, bis(isocyanatomethylthio)ethane, and 1,5-diisocyanato-2-isocyanatomethyl-3-thiapentane; sulfur-containing aromatic isocyanate compounds, such as diphenylsulfide-2,4-diisocyanate, diphenylsulfide-4,4-diisocyanate, 3,3-dimethoxy-4,4-diisocyanatodibenzyl thioether, bis(4-isocyanatomethylbenzene)sulfide, 4,4-methoxybenzenethioethylene glycol-3,3-diisocyanate, diphenyldisulfide-4,4-diisocyanate, 2,2-dimethyldiphenyldisulfide-5,5-diisocyanate, 3,3-dimethyldiphenyldisulfide-5,5-diisocyanate, 3,3-dimethyldiphenyldisulfide-6,6-diisocyanate, 4,4-dimethyldiphenyldisulfide-5,5-diisocyanate, 3,3-dimethoxydiphenyldisulfide-4,4-diisocyanate, and 4,4-dimethoxydiphenyldisulfide-3,3-diisocyanate; and sulfur-containing heterocyclic isocyanate compounds, such as 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3-dithiolane, and 4,5-bis(isocyanatomethyl)-2-methyl-1,3-dithiolane. These polyisocyanate compounds may be used alone or as a mixture of two or more thereof. Other compounds having at least one isocyanate group and/or at least one isothiocyanate group may be used alone or as a mixture of two or more thereof. Halogenated products (for example, chlorinated and brominated products) of the isocyanate compounds may also be used. Alkylated products, alkoxylated products and nitro-substituted products of the isocyanate compounds may also be used. Prepolymer modified products of the isocyanate compounds with polyhydric alcohols or thiols may also be used. Carbodiimide-, urea- and biuret-modified products of the isocyanate compounds may also be used. Dimerization or trimerization reaction products of the isocyanate compounds may also be used.

The polyisocyanate compound is preferably selected from isophorone diisocyanate (IPDI), hexamethylene diisocyanate (HDI), dicyclohexyl methanediisocyanate (H12MDI), xylylene diisocyanate (XDI), 3,8-bis(isocyanatomethyl)tricyclo[5,2,1,0$^{2,6}$]decane, 3,9-bis(isocyanatomethyl)tricyclo[5,2,1,0$^{2,6}$]decane, 4,8-bis(isocyanatomethyl)tricyclo[5,2,1,0$^{2,6}$]decane, 2,5-bis(isocyanatomethyl)bicyclo[2,2,1]heptane, 2,6-bis(isocyanatomethyl)bicyclo[2,2,1]heptane, and mixtures thereof.

The polymerizable composition of the present invention may further include a polythiol compound. The polythiol compound is not particularly limited so long as it has at least one thiol group. Examples of such polythiol compounds include bis(2-mercaptoethyl)sulfide, 4-mercaptomethyl-1,8-dimercapto-3,6-dithiaoctane, 2,3-bis(2-mercaptoethylthio)propane-1-thiol, 2,2-bis (mercaptomethyl)-1,3-propanedithiol, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropanyl)sulfide, bis(2,3-dimercaptopropanyl)disulfide, 1,2-bis(2-mercaptoethylthio)-3-mercaptopropane, 1,2-bis(2-(2-mercaptoethylthio)-3-mercaptopropylthio)ethane, bis(2-(2-mercaptoethylthio)-3-mercaptopropyl)sulfide, bis(2-(2-mercaptoethylthio)-3-mercaptopropyl)disulfide, 2-(2-mercaptoethylthio)-3-2-mercapto-3-[3-mercapto-2-(2-mercaptoethylthio)-propylthio]propylthiopropane-1-thiol, 2,2-bis(3-mercaptopropionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, 3-(3-mercapto-2-((2-mercaptoethyl)thio)propyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaerythritol tetrakis(2-mercaptoacetate), bispentaerythritol-ether-hexakis(3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, and 2-(2,2-bis(mercaptodimethylthio)ethyl)-1,3-dithietane. These polythiol compounds may be used alone or as a mixture of two or more thereof. As the polythiol compound, there may also be used, for example, a polymerization modified product obtained by prepolymerization with an isocyanate compound, a thioepoxy compound, a thietane compound, or a compound having an unsaturated bond as a resin modifier.

The polythiol compound is preferably bis(2-mercaptoethyl)sulfide or a mixture of bis(2-mercaptoethyl)sulfide and one or more other polythiol compounds.

The polymerizable composition of the present invention may further include an internal release agent. The internal release agent is preferably an acidic phosphate compound. The acidic phosphate compound is prepared by adding 2 to 3 moles of an alcoholic compound to phosphorus pentoxide ($P_2O_5$). The phosphate compound may take various forms depending on the kind of the alcohol used. Representative phosphate compounds are those in which ethylene oxide or propylene oxide is added to an aliphatic alcohol or nonylphenol group. When the polymerizable composition of the present invention includes an ethylene oxide or propylene oxide-addition phosphate compound as the internal release agent, an optical material with good releasability and high quality can be produced. The internal release agent is preferably selected from the group consisting of 4-PENPP [polyoxyethylene nonylphenol ether phosphate (5% by weight of 5-mol ethylene oxide adduct, 80% by weight of 4-mol ethylene oxide adduct, 10% by weight of 3-mol ethylene oxide adduct, and 5% by weight of 1-mol ethylene oxide adduct)], 8-PENPP [polyoxyethylene nonylphenol ether phosphate (3% by weight of 9-mol ethylene oxide adduct, 80% by weight of 8-mol ethylene oxide adduct, 5% by weight of 7-mol ethylene oxide adduct, 6% by weight of 6-mol ethylene oxide adduct, and 6% by weight of 5-mol ethylene oxide adduct)], 12-PENPP [polyoxyethylene nonylphenol ether phosphate (3% by weight of 13-mol ethylene oxide adduct, 80% by weight of 12-mol ethylene oxide adduct, 8% by weight of 11-mol ethylene oxide adduct, 3% by weight of 9-mol ethylene oxide adduct, and 6% by weight of 4-mol ethylene oxide adduct)], 16-PENPP [polyoxyethylene nonylphenol ether phosphate (3% by weight of 17-mol ethylene oxide adduct, 79% by weight of 16-mol ethylene oxide adduct, 10% by weight of 15-mol ethylene oxide adduct, 4% by weight of 14-mol ethylene oxide adduct, and 4% by weight of 13-mol ethylene oxide adduct)], 20-PENPP [polyoxyethylene nonylphenol ether phosphate (5% by weight of 21-mol ethylene oxide adduct, 78% by weight of 20-mol ethylene oxide adduct, 7% by weight of 19-mol ethylene oxide adduct, 6% by weight of 18-mol ethylene oxide adduct, and 4% by weight of 17-mol ethylene oxide adduct)], 4-PPNPP [polyoxypropylene nonylphenol ether phosphate (5% by weight of 5-mol propylene oxide adduct, 80% by weight of 4-mol propylene oxide adduct, 10% by weight of 3-mol propylene oxide adduct, and 5% by weight of 1-mol propylene oxide adduct)], 8-PPNPP [polyoxypropylene nonylphenol ether phosphate (3% by weight of 9-mol propylene oxide adduct, 80% by weight of 8-mol propylene oxide adduct, 5% by weight of 7-mol propylene oxide adduct, 6% by weight of 6-mol propylene oxide adduct, and 6% by weight of 5-mol propylene oxide adduct)], 12-PPNPP [polyoxypropylene nonylphenol ether phosphate (3% by weight of 13-mol propylene oxide adduct, 80% by weight of 12-mol propylene oxide adduct, 8% by weight of 11-mol propylene oxide adduct, 3% by weight of 9-mol propylene oxide adduct, and 6% by weight of 4-mol propylene oxide adduct)], 16-PPNPP [polyoxypropylene nonylphenol ether phosphate (3% by weight of 17-mol propylene oxide adduct, 79% by weight of 16-mol propylene oxide adduct, 10% by weight of 15-mol propylene oxide adduct, 4% by weight of 14-mol propylene oxide adduct, and 4% by weight of 13-mol propylene oxide adduct)], 20-PPNPP [polyoxypropylene nonylphenol ether phosphate (5% by weight of 21-mol propylene oxide adduct, 78% by weight of 20-mol propylene oxide adduct, 7% by weight of 19-mol propylene oxide adduct, 6% by weight of 18-mol propylene oxide adduct, and 4% by weight of 17-mol propylene oxide adduct)], Zelec UN™, and mixtures thereof. Various substituted products of the phosphate compounds, including halogenated products of the phosphate compounds, may also be used for the same purpose.

The polymerizable composition of the present invention may further include an olefinic compound as a reactive resin modifier for the purpose of controlling impact resistance, specific gravity and monomer viscosity to improve the optical properties of a copolymer optical resin (optical material). Examples of such olefinic compounds include, but are not limited to: (meth)acrylate compounds, such as benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidyl methacrylate, phenoxyethyl acrylate, phenoxyethyl methacrylate, phenyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol diacrylate, polyethylene glycol dimethacrylate, neopentyl glycol diacrylate, neopentyl glycol dimethacrylate, ethylene glycol bisglycidyl acrylate, ethylene glycol bisglycidyl methacrylate, bisphenol A diacrylate, bisphenol A dimethacrylate, 2,2-bis(4-acryloxyethoxyphenyl)propane, 2,2-bis(4-methacryloxyethoxyphenyl)propane, 2,2-bis(4-acryl oxydiethoxyphenyl)propane, 2,2-bis(4-methacryloxydiethoxyphenyl)propane, bisphenol F diacrylate, bisphenol F dimethacrylate, 1,1-bis(4-acryloxyethoxyphenyl)methane, 1,1-bis(4-methacryloxyethoxyphenyl)methane, 1,1-bis(4-acryloxydiethoxyphenyl)methane, 1,1-bis(4-methacryloxydiethoxyphenyl)methane, dimethyloltricyclodecane diacrylate, trimethylolpropane triacrylate, trimethylolpropane trimethacrylate, glycerol diacrylate, glycerol dimethacrylate, pentaerythritol triacrylate, pentaerythritol tetraacrylate, pentaerythritol tetramethacrylate, methylthioacrylate, methylthiomethacrylate, phenylthioacrylate, benzylthiomethacrylate, xylylene dithiol diacrylate, xylylene dithiol dimethacrylate, mercaptoethyl sulfide diacrylate, and mercaptoethyl sulfide dimethacrylate; allyl compounds, such as allyl glycidyl ether, diallyl phthalate, diallyl terephthalate, diallyl isophthalate, diallyl carbonate, and diethylene glycol bisallyl carbonate; and vinyl compounds, such as styrene, chlorostyrene, methylstyrene, bromostyrene, dibromostyrene, divinylbenzene, and 3,9-divinyl spiro-bi(meta-dioxane). These olefinic compounds may be used alone or as a mixture of two or more thereof.

The present invention also provides an optical material produced by casting polymerization of the polymerizable composition. Specifically, the optical material of the present invention is produced by filling and polymerizing the polymerizable composition in a mold retained by a gasket or tape. If necessary, the polymerizable composition may be degassed under reduced pressure or filtered under positive or negative pressure depending on the required physical properties of a plastic lens to be manufactured. The polymerization conditions are strongly dependent on the polymerizable composition, the kind and amount of a catalyst used, and the shape of the mold. For example, the polymerization may be carried out at a temperature of about −50 to about 150° C. for 1 to 50 hours, but is not limited to these conditions. It is preferred to cure the polymerizable composition for 1 to 48 hours while maintaining or slowly increasing the temperature in the range of 10 to 150° C.

After curing, the copolymer of the thioepoxy compound, the isocyanate compound and the thiol compound may be subjected to a suitable thermal treatment such as annealing, if required. The thermal treatment is usually carried out at a temperature between 50 and 150° C., preferably between 90 and 140° C.

Preferably, an acidic phosphate compound as an internal release agent is added to the composition of the present invention before casting polymerization. The acidic phosphate compound is the same as that described above. One or more additives used in known molding methods may be added during polymerization according to the intended purposes. Examples of such additives include chain extenders, crosslinkers, light stabilizers, UV absorbers, antioxidants, anti-coloring agents, oil soluble dyes, fillers, and adhesion promoters. Particularly, a catalyst plays an important role in curing the polymerizable composition of the present invention. Typical catalysts are epoxy curing agents. Amine compounds may also be used. Care needs to be taken in using strong amines that react violently with the isocyanate. In the present invention, acid salts of amines, phosphonium salts, phosphines, and tertiary amines having no electron withdrawing groups, Lewis acids, and radical initiators are mainly used. The kind and amount of the catalyst may vary according to the intended applications.

The copolymer resin of the present invention may be manufactured into various molded products by changing the mold for casting polymerization. The copolymer resin can be used as a material for various optical products such as spectacle lenses, camera lenses and light emitting diodes (LEDs). The copolymer resin is particularly suitable for use in the manufacture of optical devices, as well as optical products such as spectacle lenses, camera lenses and light emitting diodes (LEDs).

The present invention also provides a plastic lens using the copolymer resin. The plastic lens of the present invention may include coating layers at one or both sides thereof, if needed. Examples of the coating layers include primer layers, hard coat layers, antireflective layers, antifogging coating layers, antifouling coating layers, and water-repellent layers. These coating layers may be formed singly or may be combined to form a multilayer structure. The coating layers formed at both sides of the plastic lens may be the same as or different from each other.

EXAMPLES

The following examples are provided for illustrative purposes only and are not intended to limit the scope of the present invention.

Test and Evaluation Methods

The YI values of resins were measured using a UV-Vis spectrophotometer (Model UV-2450, SHIMADZU) fitted with an IRS-2200 condenser. For the measurement, the YI of air was used as the reference and each resin was fixed to a lens clamp. YI represents yellowness index and can be measured using a colorimeter. A lower YI indicates a better color. The color of a resin was judged to be "poor (x)" when the YI value of the resin was different by +1 or more from that of a resin obtained in Example 1, and "good (o)" when the difference in YI value was smaller than +1.

Refractive indices (nE) and Abbe numbers were measured using Abbe refractometer models IT and DR-M4 (Atago) at 20° C.

Synthesis Example 1

Synthesis of bis(3-chloro-2-hydroxypropyl)sulfide (BCPS)

Epichlorohydrin (5563 g, 60.12 mol) and methanol (2500 g) were put into a 10-liter reactor. The reaction temperature was adjusted to 6° C. When the reaction temperature reached 6° C., sodium hydroxide (50% aq., 5 g) was added to the mixture. NaSH.xH$_2$O (70% NaSH, 3660 g, 45.75 mol), methanol (1000 g) and water (500 g) were completely dissolved with stirring in another 10-liter reactor, and hydrochloric acid was slowly added dropwise thereto to generate hydrogen sulfide gas. The hydrogen sulfide gas was added to the epichlorohydrin solution to obtain bis(3-chloro-2-hydroxypropyl)sulfide. The completion of the reaction was defined as the time when epichlorohydrin and 3-chloro-2-hydroxypropane-1-thiol disappeared completely and bis(3-chloro-2-hydroxypropyl)sulfide was formed, which was confirmed by GC. When 3-chloro-2-hydroxy-propane-1-thiol was present, the content of the thiol compound was calculated from the relative integral ratio by GC and epichlorohydrin was further added in an amount corresponding to the calculated content. The reaction of epichlorohydrin and the thiol compound afforded bis(3-chloro-2-hydroxypropyl)sulfide (BCPS).

Synthesis Example 2

Synthesis of bis(3-chloro-2-hydroxypropyl)disulfide (BCPDS)

Epichlorohydrin (5563 g, 60.12 mol) and methanol (2500 g) were put into a 10-liter reactor. The reaction temperature was adjusted to 5° C. When the reaction temperature reached 5° C., sodium hydroxide (50% aq., 5 g) was added to the mixture. NaSH.xH$_2$O (70% NaSH, 3660 g, 45.75 mol), methanol (1000 g) and water (500 g) were completely dissolved with stirring in another 10-liter reactor, and hydrochloric acid was slowly added dropwise thereto to generate hydrogen sulfide gas. The hydrogen sulfide gas was added to the epichlorohydrin solution to obtain 3-chloro-2-hydroxy-propane-1-thiol. The reaction was stopped when epichlorohydrin disappeared completely and 3-chloro-2-hydroxy-propane-1-thiol was formed, which was confirmed by GC. The reaction mixture was distilled under reduced pressure to obtain 6550 g of 3-chloro-2-hydroxy-propane-1-thiol. The 3-chloro-2-hydroxy-propane-1-thiol (1500 g, 11.85 mol) and methanol (1500 g) were put into a reactor. The mixture was cooled to 10° C., and then 35% hydrogen peroxide (575.61 g, 5.92 mol) was slowly added thereto dropwise, affording bis(3-chloro-2-hydroxypropyl)disulfide (BCPDS).

Synthesis Example 3

Synthesis of bis(2,3-epithiopropyl)sulfide (BEPS-1)

1072.48 g (8.47 mol) of bis(3-chloro-2-hydroxypropyl)sulfide, 1300 g of toluene, and 800 g of methanol were put into a 10-liter reactor. The reaction temperature was adjusted to 30° C. with stirring. When the reaction temperature reached 25° C., NaOH (50% aq., 783.08 g, 9.78 mol) was added dropwise within 1 h. The reaction was carried out while maintaining a temperature of 35-37° C. After standing at 37° C. for about 30 min, 2000 g of toluene was added to the reaction mixture, followed by stirring for about 10 min. The resulting mixture was left standing for layer separation. The upper organic layer was washed twice with water, and then the water was removed as much as possible. To the organic layer was added 400 g of methanol. After stirring, thiourea (1117.65 g, 14.30 mol) and acetic anhydride (70 g) were added at a temperature of 8° C. The reaction was continued at 18° C. for 18 h. The reaction was stopped when almost all the starting materials disappeared, which was confirmed by HPLC, and the content of 2,3-epoxypropyl(2,3-epithiopropyl)sulfide reached 6%, which was confirmed by GC analysis. After completion of the reaction, stirring was stopped for layer separation. The obtained organic layer was washed three times with water and the organic solvent was removed, affording bis(2,3-epithiopropyl)sulfide. The product had a refractive index (nD, 20° C.) of 1.618.

Synthesis Example 4

Synthesis of bis(2,3-epithiopropyl)sulfide (BEPS-2)

1072.48 g (8.47 mol) of bis(3-chloro-2-hydroxypropyl)sulfide, 1300 g of toluene, and 800 g of methanol were put into a 10-liter reactor. The reaction temperature was adjusted to 30° C. with stirring. When the reaction temperature reached 25° C., NaOH (50% aq., 783.08 g, 9.78 mol) was added dropwise within 1 h. The reaction was carried out while maintaining a temperature of 35-37° C. After standing at 37° C. for about 30 min, 2000 g of toluene was added to the reaction mixture, followed by stirring for about 10 min. The resulting mixture was left standing for layer separation. The upper organic layer was washed twice with water, and then the water was removed as much as possible. To the organic layer was added 400 g of methanol. After stirring, thiourea (1117.65 g, 14.30 mol) and acetic anhydride (70 g) were added at a temperature of 8° C. The reaction was continued at 18° C. for 18 h. The reaction was stopped when almost all the starting materials disappeared, which was confirmed by HPLC, and the content of 2,3-epoxypropyl(2,3-epithiopropyl)sulfide reached 9%, which was confirmed by GC analysis. After completion of the reaction, stirring was stopped for layer separation. The obtained organic layer was washed three times with water and the organic solvent was removed, affording bis(2,3-epithiopropyl)sulfide. The product had a refractive index (nD, 20° C.) of 1.614.

Synthesis Example 5

Synthesis of bis(2,3-epithiopropyl)sulfide (BEPS-3)

1072.48 g (8.47 mol) of bis(3-chloro-2-hydroxypropyl)sulfide, 1300 g of toluene, and 800 g of methanol were put into a 10-liter reactor. The reaction temperature was adjusted to 30° C. with stirring. When the reaction temperature reached 25° C., NaOH (50% aq., 783.08 g, 9.78 mol) was added dropwise within 1 h. The reaction was carried out while maintaining a temperature of 35-37° C. After standing at 37° C. for about 30 min, 2000 g of toluene was added to the reaction mixture, followed by stirring for about 10 min. The resulting mixture was left standing for layer separation. The upper organic layer was washed twice with water, and then the water was removed as much as possible. To the organic layer was added 400 g of methanol. After stirring, thiourea (1117.65 g, 14.30 mol) and acetic anhydride (70 g) were added at a temperature of 8° C. The reaction was continued at 18° C. for 18 h. The reaction was stopped when almost all the starting materials disappeared, which was confirmed by HPLC, and the content of 2,3-epoxypropyl(2,3-epithiopropyl)sulfide reached 14%, which was confirmed by GC analysis. After completion of the reaction, stirring was stopped for layer separation. The obtained organic layer was washed three times with water and the organic solvent was removed, affording bis(2,3-epithiopropyl)sulfide. The product had a refractive index (nD, 20° C.) of 1.611.

Synthesis Example 6

Synthesis of bis(2,3-epithiopropyl)disulfide (BEPDS)

1229.34 g (4.89 mol) of bis(3-chloro-2-hydroxypropyl) disulfide, 1300 g of toluene, and 800 g of methanol were put into a 10-liter reactor. The reaction temperature was adjusted to 30° C. with stirring. When the reaction temperature reached 25° C., NaOH (50% aq., 783.08 g, 9.78 mol) was added dropwise within 1 h. The reaction was carried out while maintaining a temperature of 35-37° C. After standing at 37° C. for about 30 min, 2000 g of toluene was added to the reaction mixture, followed by stirring for about 10 min. The resulting mixture was left standing for layer separation. The upper organic layer was washed twice with water, and then the water was removed as much as possible. To the organic layer was added 400 g of methanol. After stirring, thiourea (1117.65 g, 14.30 mol) and acetic anhydride (70 g) were added at a temperature of 8° C. The reaction was continued at 18° C. for 18 h. The reaction was stopped when almost all the starting materials disappeared, which was confirmed by HPLC, and the content of 2,3-epoxypropyl(2,3-epithiopropyl)disulfide reached 10%, which was confirmed by GC analysis. After completion of the reaction, stirring was stopped for layer separation. The obtained organic layer was washed three times with water and the organic solvent was removed, affording bis(2,3-epithiopropyl)disulfide (BEPDS). The product had a refractive index (nD, 20° C.) of 1.631.

Comparative Synthesis Example 1

Synthesis of bis(2,3-epithiopropyl)sulfide (BEPS-4)

1072.48 g (8.47 mol) of bis(3-chloro-2-hydroxypropyl) sulfide, 1300 g of toluene, and 800 g of methanol were put into a 10-liter reactor. The reaction temperature was adjusted to 30° C. with stirring. When the reaction temperature reached 25° C., NaOH (50% aq., 783.08 g, 9.78 mol) was added dropwise within 1 h. The reaction was carried out while maintaining a temperature of 35-37° C. After standing at 37° C. for about 30 min, 2000 g of toluene was added to the reaction mixture, followed by stirring for about 10 min. The resulting mixture was left standing for layer separation. The upper organic layer was washed twice with water, and then the water was removed as much as possible. To the organic layer was added 400 g of methanol. After stirring, thiourea (1117.65 g, 14.30 mol) and acetic anhydride (70 g) were added at a temperature of 8° C. The reaction was continued at 18° C. for 18 h. The reaction was stopped when almost all the starting materials disappeared, which was confirmed by HPLC, and the content of 2,3-epoxypropyl(2,3-epithiopropyl)sulfide reached 3.5%, which was confirmed by GC analysis. After completion of the reaction, stirring was stopped for layer separation. The obtained organic layer was washed three times with water and the organic solvent was removed, affording bis(2,3-epithiopropyl)sulfide. The product had a refractive index (nD, 20° C.) of 1.623.

Comparative Synthesis Example 2

Synthesis of bis(2,3-epithiopropyl)sulfide (BEPS-5)

1072.48 g (8.47 mol) of bis(3-chloro-2-hydroxypropyl) sulfide, 1300 g of toluene, and 800 g of methanol were put into a 10-liter reactor. The reaction temperature was adjusted to 30° C. with stirring. When the reaction temperature reached 25° C., NaOH (50% aq., 783.08 g, 9.78 mol) was added dropwise within 1 h. The reaction was carried out while maintaining a temperature of 35-37° C. After standing at 37° C. for about 30 min, 2000 g of toluene was added to the reaction mixture, followed by stirring for about 10 min. The resulting mixture was left standing for layer separation. The upper organic layer was washed twice with water, and then the water was removed as much as possible. To the organic layer was added 400 g of methanol. After stirring, thiourea (1117.65 g, 14.30 mol) and acetic anhydride (70 g) were added at a temperature of 8° C. The reaction was continued at 18° C. for 18 h. The reaction was stopped when almost all the starting materials disappeared, which was confirmed by HPLC, and the content of 2,3-epoxypropyl(2,3-epithiopropyl)sulfide reached 16%, which was confirmed by GC analysis. After completion of the reaction, stirring was stopped for layer separation. The obtained organic layer was washed three times with water and the organic solvent was removed, affording bis(2,3-epithiopropyl)sulfide. The product had a refractive index (nD, 20° C.) of 1.607.

Example 1

89 g of the bis(2,3-epithiopropyl)sulfide (BEPS-1) prepared in Synthesis Example 3 as a thioepoxy compound, 5 g of isophorone diisocyanate as an isocyanate compound, 6 g of bis(2-mercaptoethyl)sulfide as a thiol compound, 0.15 g of 8-PENPP as an internal release agent, 0.2 g of tetrabutylphosphonium bromide, 0.1 g of triphenylphosphine, HTAQ (20 ppm) and PRD (10 ppm) as organic dyes, and 1.5 g of HOPBT as a UV absorber were mixed and dissolved at 20° C. to prepare a homogeneous solution. 8-PENPP refers to polyoxyethylene nonylphenol ether phosphate (3% by weight of 9-mol ethylene oxide adduct, 80% by weight of 8-mol ethylene oxide adduct, 5% by weight of 7-mol ethylene oxide adduct, 6% by weight of 6-mol ethylene oxide adduct, and 6% by weight of 5-mol ethylene oxide adduct) as a phosphoric acid ester. The solution was degassed at 400 Pa for 1 h, filtered through a 1 μm PTFE filter, and filled in a mold composed of a glass mold and a tape. After the mold was charged into a polymerization oven, the temperature was slowly raised from 25-130° C. over 21 h. After completion of the polymerization, the mold was taken out of the oven. Releasability of the molded product from the mold was good. The obtained resin was annealed at 130° C. for 4 h. The annealed resin was measured to have a refractive index (nE) of 1.699 and an Abbe number of 35. The state of the solution before filling in the mold was visually observed, and an observation was made as to whether ring-shaped defects were formed on the surface of the molded product after demolding. As a result, no abnormalities were observed and no whitening appeared. The resin had a YI value of 1.61 and was stable in quality.

Examples 2-4

Compositions were prepared and optical lenses were manufactured in the same manner as in Example 1, except that the compounds and their amounts were changed as shown in Table 1. The physical properties of the lenses were evaluated, and the results are shown in Table 1.

Comparative Examples 1-2

Compositions were prepared and optical lenses were manufactured in the same manner as in Example 1, except that the compounds and their amounts were changed as shown in Table 1. The physical properties of the lenses were evaluated, and the results are shown in Table 1.

TABLE 1

| Example No. | Thioepoxy compound | Isocyanate compound | Thiol compound | Refractive index (nE) | Releasability | Color |
|---|---|---|---|---|---|---|
| Example 1 | BEPS-1 89 g | IPDI 5 g | BMES 6 g | 1.699 | ○ | ○ |
| Example 2 | BEPS-2 89 g | IPDI 5 g | BMES 6 g | 1.697 | ○ | ○ |
| Example 3 | BEPS-3 89 g | IPDI 5 g | BMES 6 g | 1.695 | ○ | ○ |
| Example 4 | BEPDS 91 g | IPDI 4 g | BMES 5 g | 1.738 | ○ | ○ |
| Comparative Example 1 | BEPS-4 89 g | IPDI 5 g | BMES 6 g | 1.702 | ○ | x |
| Comparative Example 2 | BEPS-5 89 g | IPDI 5 g | BMES 6 g | 1.687 | x | ○ |

<Abbreviations>
Monomers
BEPS: Bis(2,3-epithiopropyl)sulfide
BEPDS: Bis(2,3-epithiopropyl)disulfide
BMES: Bis(2-mercaptoethyl)sulfide
IPDI: Isophorone diisocyanate
HOPBT: 2-(2'-Hydroxy-5'-t-octylphenyl)-2H-benzotriazole
TBPB: Tetrabutylphosphonium bromide
HTQA: 1-Hydroxy-4-(p-toluidine)anthraquinone
PRD: Perinone dye

The invention claimed is:

1. A polymerizable composition comprising a thioepoxy compound (A) and a compound (B) formed as a by-product in the preparation of the thioepoxy compound (A) wherein the compound (B) is at least one of 2,3-epoxypropyl(2,3-epithiopropyl)sulfide and 2,3-epoxypropyl(2,3-epithiopropyl)disulfide represented by Formula 1 and is present in an amount of 4.5 to 15% of the total weight of the compounds (A) and (B):

[Formula 1]

$$\underset{(X=S,\ S-S)}{\triangle\hspace{-0.2em}\diagup\hspace{-0.3em}\diagdown\hspace{-0.2em}X\hspace{-0.2em}\diagup\hspace{-0.3em}\diagdown\hspace{-0.2em}S\hspace{-0.2em}\diagup\hspace{-0.3em}\diagdown\hspace{-0.2em}\triangle}$$

2. The polymerizable composition according to claim 1, further comprising a phosphonium salt as a polymerization catalyst.

3. The polymerizable composition according to claim 1, further comprising a polyisocyanate compound.

4. The polymerizable composition according to claim 1, further comprising a polythiol compound.

5. The polymerizable composition according to claim 1, further comprising a polyisocyanate compound, a polythiol compound, and a phosphonium salt as a polymerization catalyst.

6. The polymerizable composition according to claim 1, wherein the thioepoxy compound is selected from the group consisting of bis(2,3-epithiopropyl)sulfide, bis(2,3-epithiopropyl)disulfide, 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, 2,5-bis(β-epithiopropylthiomethyl)-1,4-dithiane, 2,5-bis(β-epithiopropylthioethylthiomethyl)-1,4-dithiane, 2-(2-β-epithiopropylthioethylthio)-1,3-bis (β-epithiopropylthio) propane, and mixtures thereof.

7. The polymerizable composition according to claim 3, wherein the polyisocyanate compound is selected from the group consisting of isophorone diisocyanate, hexamethylene diisocyanate, dicyclohexyl methanediisocyanate, xylylene diisocyanate, 3,8-bis(isocyanatomethyl)tricyclo[5,2,1,0$^{2,6}$] decane, 3,9-bis(isocyanatomethyl)tricyclo[5,2,1,0$^{2,6}$]decane, 4,8-bis(isocyanatomethyl)tricyclo [5,2,1,0$^{2,6}$]decane, 2,5-bis(isocyanatomethyl)bicyclo[2,2,1]heptane, 2,6-bis(isocyanatomethyl)bicyclo[2,2,1]heptane, and mixtures thereof.

8. The polymerizable composition according to claim 4, wherein the polythiol compound is bis(2-mercaptoethyl)sulfide.

9. The polymerizable composition according to claim 1, further comprising an olefinic compound as a reactive resin modifier.

10. The polymerizable composition according to claim 1, further comprising, as an internal release agent, at least one phosphate compound selected from the group consisting of 4-PENPP [polyoxyethylene nonylphenol ether phosphate (5% by weight of 5-mol ethylene oxide adduct, 80% by weight of 4-mol ethylene oxide adduct, 10% by weight of 3-mol ethylene oxide adduct, and 5% by weight of 1-mol ethylene oxide adduct)], 8-PENPP [polyoxyethylene nonylphenol ether phosphate (3% by weight of 9-mol ethylene oxide adduct, 80% by weight of 8-mol ethylene oxide adduct, 5% by weight of 7-mol ethylene oxide adduct, 6% by weight of 6-mol ethylene oxide adduct, and 6% by weight of 5-mol ethylene oxide adduct)], 12-PENPP [polyoxyethylene nonylphenol ether phosphate (3% by weight of 13-mol ethylene oxide adduct, 80% by weight of 12-mol ethylene oxide adduct, 8% by weight of 11-mol ethylene oxide adduct, 3% by weight of 9-mol ethylene oxide adduct, and 6% by weight of 4-mol ethylene oxide adduct)], 16-PENPP [polyoxyethylene nonylphenol ether phosphate (3% by weight of 17-mol ethylene oxide adduct, 79% by weight of 16-mol ethylene oxide adduct, 10% by weight of 15-mol ethylene oxide adduct, 4% by weight of 14-mol ethylene oxide adduct, and 4% by weight of 13-mol ethylene oxide adduct)], 20-PENPP [polyoxyethylene nonylphenol ether phosphate (5% by weight of 21-mol ethylene oxide adduct, 78% by weight of 20-mol ethylene oxide adduct, 7% by weight of 19-mol ethylene oxide adduct, 6% by weight of 18-mol ethylene oxide adduct, and 4% by weight of 17-mol ethylene oxide adduct)], 4-PPNPP [polyoxypropylene nonylphenol ether phosphate (5% by weight of 5-mol propylene oxide adduct, 80% by weight of 4-mol propylene oxide adduct, 10% by weight of 3-mol propylene oxide adduct, and 5% by weight of 1-mol propylene oxide adduct)], 8-PPNPP [polyoxypropylene nonylphenol ether phosphate (3% by weight of 9-mol propylene oxide adduct, 80% by weight of 8-mol propylene oxide adduct, 5% by weight of 7-mol propylene oxide adduct, 6% by weight of 6-mol propylene oxide adduct, and 6% by weight of 5-mol propylene oxide adduct)], 12-PPNPP [polyoxypropylene nonylphenol ether phosphate (3% by weight of 13-mol propylene oxide adduct, 80% by weight of 12-mol propylene oxide adduct, 8% by weight of 11-mol propylene oxide adduct, 3% by weight of 9-mol propylene oxide adduct, and 6% by weight of 4-mol propylene oxide adduct)], 16-PPNPP [polyoxypropylene nonylphenol ether phosphate (3% by weight of 17-mol propylene oxide adduct, 79% by weight of 16-mol propylene oxide adduct, 10% by weight of 15-mol propylene oxide adduct, 4% by weight of 14-mol propylene oxide adduct, and 4% by weight of 13-mol propylene oxide adduct)], and 20-PPNPP [polyoxypropylene nonylphenol ether phosphate (5% by weight of 21-mol propylene oxide adduct, 78% by weight of 20-mol propylene oxide adduct, 7% by weight of 19-mol propylene oxide adduct, 6% by weight of 18-mol propylene oxide adduct, and 4% by weight of 17-mol propylene oxide adduct)].

11. A method for producing a thioepoxy optical material, comprising polymerizing the polymerizable composition according to claim 1.

12. The method according to claim 11, wherein the thioepoxy compound (A) is selected from the group consisting of bis(2,3-epithiopropyl)sulfide, bis(2,3-epithiopropyl)disulfide, 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, 2,5-bis(β-epithiopropylthiomethyl)-1,4-dithiane, 2,5-bis(β-epithiopropylthioethylthiomethyl)-1,4-dithiane, 2-(2-(β-epithiopropylthioethylthio)-1,3-bis(β-epithiopropylthio)propane, and mixtures thereof.

13. The method according to claim 11, wherein the polymerizable composition further comprises a phosphonium salt as a polymerization catalyst.

14. The method according to claim 11, wherein the polymerizable composition further comprises bis(2-mercaptoethyl)sulfide as a polythiol compound.

15. The method according to claim 11, wherein the polymerizable composition further comprises, as an internal release agent, at least one phosphate compound selected from the group consisting of 4-PENPP [polyoxyethylene nonylphenol ether phosphate (5% by weight of 5-mol ethylene oxide adduct, 80% by weight of 4-mol ethylene oxide adduct, 10% by weight of 3-mol ethylene oxide adduct, and 5% by weight of 1-mol ethylene oxide adduct)], 8-PENPP [polyoxyethylene nonylphenol ether phosphate (3% by weight of 9-mol ethylene oxide adduct, 80% by weight of 8-mol ethylene oxide adduct, 5% by weight of 7-mol ethylene oxide adduct, 6% by weight of 6-mol ethylene oxide adduct, and 6% by weight of 5-mol ethylene oxide adduct)], 12-PENPP [polyoxyethylene nonylphenol ether phosphate (3% by weight of 13-mol ethylene oxide adduct, 80% by weight of 12-mol ethylene oxide adduct, 8% by weight of 11-mol ethylene oxide adduct, 3% by weight of 9-mol ethylene oxide adduct, and 6% by weight of 4-mol ethylene oxide adduct)], 16-PENPP [polyoxyethylene nonylphenol ether phosphate (3% by weight of 17-mol ethylene oxide adduct, 79% by weight of 16-mol ethylene oxide adduct, 10% by weight of 15-mol ethylene oxide adduct, 4% by weight of 14-mol ethylene oxide adduct, and 4% by weight of 13-mol ethylene oxide adduct)], 20-PENPP [polyoxyethylene nonylphenol ether phosphate (5% by weight of 21-mol ethylene oxide adduct, 78% by weight of 20-mol ethylene oxide adduct, 7% by weight of 19-mol ethylene oxide adduct, 6% by weight of 18-mol ethylene oxide adduct, and 4% by weight of 17-mol ethylene oxide adduct)], 4-PPNPP [polyoxypropylene nonylphenol ether phosphate (5% by weight of 5-mol propylene oxide adduct, 80% by weight of 4-mol propylene oxide adduct, 10% by weight of 3-mol propylene oxide adduct, and 5% by weight of 1-mol propylene oxide adduct)], 8-PPNPP [polyoxypropylene nonylphenol ether phosphate (3% by weight of 9-mol propylene oxide adduct, 80% by weight of 8-mol propylene oxide adduct, 5% by weight of 7-mol propylene oxide adduct, 6% by weight of 6-mol propylene oxide adduct, and 6% by weight of 5-mol propylene oxide adduct)], 12-PPNPP [polyoxypropylene nonylphenol ether phosphate (3% by weight of 13-mol propylene oxide adduct, 80% by weight of 12-mol propylene oxide adduct, 8% by weight of 11-mol propylene oxide adduct, 3% by weight of 9-mol propylene oxide adduct, and 6% by weight of 4-mol propylene oxide adduct)], 16-PPNPP [polyoxypropylene nonylphenol ether phosphate (3% by weight of 17-mol propylene oxide adduct, 79% by weight of 16-mol propylene oxide adduct, 10% by weight of 15-mol propylene oxide adduct, 4% by weight of 14-mol propylene oxide adduct, and 4% by weight of 13-mol propylene oxide adduct)], and 20-PPNPP [polyoxypropylene nonylphenol ether phosphate (5% by weight of 21-mol propylene oxide adduct, 78% by weight of 20-mol propylene oxide adduct, 7% by weight of 19-mol propylene oxide adduct, 6% by weight of 18-mol propylene oxide adduct, and 4% by weight of 17-mol propylene oxide adduct)].

16. A thioepoxy optical material obtained by polymerization of the polymerizable composition according to claim 1.

17. An optical lens composed of the optical material according to claim 16.

* * * * *